United States Patent

Li et al.

[11] Patent Number: 5,874,311
[45] Date of Patent: Feb. 23, 1999

[54] METHOD FOR DIFFERENTIATION OF RETICULOCYTES IN BLOOD

[75] Inventors: Yi Li; Jing Li; Carole Young, all of Miami, Fla.

[73] Assignee: Coulter International Corp., Miami, Fla.

[21] Appl. No.: 976,226

[22] Filed: Nov. 21, 1997

[51] Int. Cl.6 ................................................ G01N 31/00
[52] U.S. Cl. .......................... 436/10; 436/63; 436/164; 436/175
[58] Field of Search ............................ 436/10, 63, 164, 436/175; 435/2

[56] References Cited

U.S. PATENT DOCUMENTS

| | | | |
|---|---|---|---|
| 4,985,174 | 1/1991 | Kuroda et al. | 252/408.1 |
| 5,125,737 | 6/1992 | Rodriguez et al. | 356/39 |
| 5,155,044 | 10/1992 | Ledis et al. | 436/17 |
| 5,389,549 | 2/1995 | Hamaguchi et al. | 436/10 |
| 5,411,891 | 5/1995 | Fan et al. | 436/63 |
| 5,492,833 | 2/1996 | Rodriguez et al. | 436/63 |
| 5,559,037 | 9/1996 | Kim et al. | 436/63 |
| 5,616,501 | 4/1997 | Rodriguez et al. | 436/63 |
| 5,686,308 | 11/1997 | Li et al. | 436/63 |
| 5,733,784 | 3/1998 | Studholme et al. | 436/63 |
| 5,737,078 | 4/1998 | Takarada et al. | 356/338 |

*Primary Examiner*—Maureen M. Wallenhorst
*Attorney, Agent, or Firm*—Mitchell E. Alter

[57] ABSTRACT

A method is provided for differentiation of reticulocytes. In addition, the method provides for a concurrent differentiation of leukocyte subpopulations in a blood cell sample by suitable electronic and optical measurements. The method includes exposing a blood cell sample to a reagent system to lyse mature red blood cells and subsequently analyzing reticulocytes in a flow cell by optical analysis. A concurrent differentiation of reticulocytes and leukocytes can be performed using electronic and optical analysis. The electronic and optical analysis includes light scatter and impedance measurements. This method does not require the use of nuclear stain for differentiation of reticulocytes.

9 Claims, 3 Drawing Sheets

# METHOD FOR DIFFERENTIATION OF RETICULOCYTES IN BLOOD

FIELD OF THE INVENTION

The present invention relates to a method which differentiates reticulocytes from other cell types in a blood cell sample by using light scatter measurement. In addition, the method provides for a concurrent differentiation of leukocytes in a blood cell sample by suitable electronic and optical measurements.

BACKGROUND OF THE INVENTION

The red blood cell goes through six stages of development: pronormoblast, basophilic normoblast, polychromatophilic blast, orthochromic normoblast, reticulocyte, and mature red blood cell. The first four stages are normally confined to the bone marrow. The reticulocytes, however, are found in both the bone marrow and peripheral blood. Increased reticulocytes are found in hemolytic anemias, thalassemia, sideroblastic anemia, and in acute and chronic blood loss. Therefore, it is of clinical importance to analyze reticulocytes contained in a blood sample. Traditionally, reticulocyte measurement is performed manually. The process involves the smearing of a blood sample stained by new methylene blue dye on a microscope slide, followed by manual visual analysis of the individual slide. The reticulocytes are reported as percentage of the total red blood cells in the blood sample. This approach is extremely time-consuming as well as being subjective to the interpretation of the individual analyzing the slide.

In recent years, several automated methods have been developed for analysis of reticulocytes. The majority of these methods utilize fluorescent RNA stain to specifically stain reticulocytes and use fluorescence flow cytometry for detection. U.S. Pat. No. 4,985,174 to Kuroda et al. discloses a reagent containing auramine O for the fluorescent staining of reticulocytes in a sample of whole blood to permit determination of reticulocytes by means of a flow cytometer. U.S. Pat. No. 5,411,891 to Fan et al. discloses a reagent which includes an organic cationic dye for staining the reticulocytes in the blood sample and a buffer solution for maintaining pH. The reticulocytes, mean cell volume and hemoglobin concentrations are analyzed by fluorescence flow cytometer. These methods can differentiate reticulocytes from other cell populations; however, fluorescence measurement is a complex and expensive detection method.

U.S. Pat. No. 5,616,501 to Rodriquez et al. discloses a method using upper median angle light scatter (UMALS) measurement to detect stained and ghosted reticulocytes. The method precipitates intracellular RNA of the reticulocytes by incubating the blood sample with a new methylene blue dye solution, then releases hemoglobin and fixes the red blood cells by further incubating with a ghosting reagent. In the treated sample mixture, the reticulocytes have a shift in their median angle light scatter signals, which is used to differentiate the reticulocytes from mature red blood cells. This method avoids the use of costly fluorescence measurement; however, the precipitation mechanism of the staining process can be troublesome on an instrument. In addition, the critical ghosting process requires heating of the sample mixture to 41° C. for an automated analysis.

On the other hand, analysis of leukocyte populations from whole blood samples is an integral and essential part of diagnostic procedures regarding a multiplicity of pathologies. The ability to analyze the major subpopulations of leukocytes in an automated manner is essential for a rapid diagnosis of a single blood sample and for the rapid processing of many samples at once.

U.S. Pat. No. 5,155,044 (to Ledis et al.) discloses a method for isolation and analysis of leukocytes from a whole blood sample, which enables differentiation of leukocytes into five subpopulations in a one-step measurement on an automated hematology analyzer. The detection technique involves a concurrent light scatter measurement and impedance measurements in both DC (direct current) and RF (radio frequency). Ledis et al. enables automated differentiation of leukocyte subpopulations, but they do not provide differentiation of reticulocytes.

U.S. Pat. No. 5,389,549 (to Hamaguchi et al.) describes a lysis reagent system and a method for differentiation of leukocytes into five subpopulations with a complex procedure. The method requires three lytic reagents, three separate sample preparations and measurements for the identity of eosinophil, neutrophil and basophil populations in addition to the lymphocyte and monocyte populations. Hamaguchi et al. enables automated differentiation of leukocyte subpopulations, but they do not provide differentiation of reticulocytes. U.S. Pat. No. 5,686,308 (to Li et al.) describes a lysing reagent system and a method for differentiation of leukocytes into five subpopulations in a one-step measurement on an automated hematology analyzer. The lytic reagent comprises a lytic reagent comprising an ethoxylated long chain amine compound and acid to adjust the pH of the lytic reagent to be within the range of 2.0 to 3.6; and a hypertonic, alkaline stabilizing reagent. This patent teaches a reagent and method for differentiation of leukocytes subpopulations, but does not teach differentiation of reticulocytes.

Based on the foregoing, there exists a need for a simple and less costly analysis method for differentiating reticulocytes.

SUMMARY OF THE INVENTION

One object of the present invention is to provide a method which permits the differentiation of reticulocytes on an automated hematology analyzer without using fluorescence or nuclear stain. The method comprises exposing a blood cell sample to a reagent system to lyse mature red blood cells; and analyzing said sample in a flow cell by measuring low angle light scatters to differentiate reticulocytes from other cell types.

Another object of the present invention is to provide a method which permits a concurrent differentiation of reticulocytes and leukocytes. The method comprises exposing a blood cell sample to a reagent system to lyse mature red blood cells; and analyzing said sample in a flow cell by DC and light scatter measurements to differentiate reticulocytes and leukocyte subpopulations.

As will be better appreciated from the following Detailed Description of Preferred Embodiments, the invention is particularly advantageous compared to the prior art in that it provides differentiation of reticulocytes utilizing light scatters without nuclear staining and the use of complex fluorescence detection methods. The invention will be better understood from the following description of preferred embodiments.

DETAILED DESCRIPTION OF THE PREFERRED EMBODIMENTS

Figure 1:
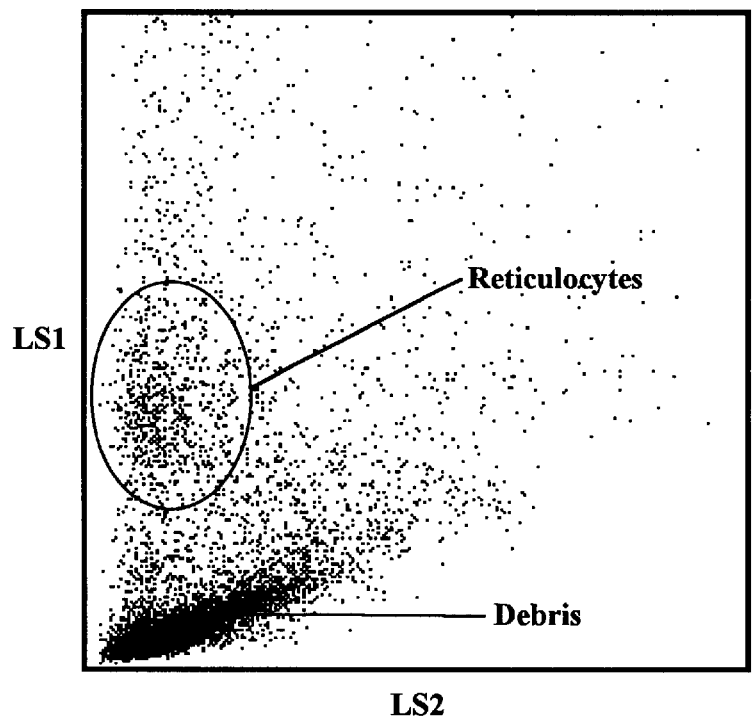
FIGS. 1–3 are scattergrams obtained in accordance with the practice of the present invention as described in Examples I to III.

The present invention relates to a method for differentiation of reticulocytes and also for a method for concurrent differentiation of leukocyte subpopulations in a blood cell sample.

In a first embodiment, the method of the present invention comprises exposing a blood cell sample to a reagent system wherein the reagent system does not contain a dye or nuclear stain to lyse mature red blood cells; and subsequently analyzing the sample mixture in a focused flow cell using light scatters to differentiate reticulocytes in the blood cell sample.

A reagent system suitable for the present invention comprises a lytic reagent comprising an ethoxylated long chain amine compound represented by the general formula:

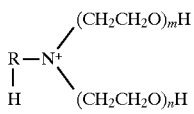

wherein R is an alkyl, alkenyl or alkynyl group having 12 to 22 carbon atoms, m and n are each 1 or more and m+n is between 20 and 40, and acid to adjust the pH of the lytic reagent to be within the range of 2.0 to 3.6; and a hypertonic, alkaline stabilizing reagent.

Optionally, one or more solubilizers can be included in the lytic reagent in an amount effective to reduce red blood cell debris. Typically, the solubilizers are polyoxyethylene and polyoxypropylene copolymers, and ethoxylated alcohols having a HLB of 16 or greater. Suitable copolymers include, but are not limited to, Pluronic copolymer (BASF Corporation, Parsippany, N.J.) such as Pluronic F38 and Pluronic 25R8, and suitable ethoxylated alcohols include, but are not limited to, Plurafac A38 (BASF) and Hetoxol STA 30 (Heterene, Inc. Paterson, N.J.)

Additional optional additives can also be included in the lytic reagent in concentrations that their presence is compatible with the primary functional components of the lytic reagent composition. Among these additives are preservatives which have anti-oxidant properties, to increase the shelf-life of the composition, and which have anti-microbial properties. Preservatives which have anti-oxidant properties include, but are not limited to,. EDTA and butylmethylphenol. Preservatives which have anti-microbial activity include but are not limited to dimethyloidimethyl hydantoin, iodopropynylbutyl carbamate and isothiozolone derivatives.

The differentiation of reticulocytes is performed in a focused flow cell with an sheath fluid using light scatter measurement. When a particle such as a blood cell passes through the aperture of a focused flow cell, it scatters the incident light from a laser beam in all directions. The light scatter signals can be detected by a light detector at various angles relative to the incident light beam between 0° to 180°. Each cell population has different light scattering properties, either significant or minor, which might be utilized for differentiation of different cell populations. The light scatter signals detected in less than 10° from the incident light is commonly called low angle light scatter, which closely correlates to cell size as well as contents of a cell.

Light scatter signal from a particle or a cell passing through the flow cell is used for the purposes of the present invention. Preferably, two angles of light scatter signals are used for differentiation of reticulocytes. More preferably, both angles of light scatter are less than 10°. The more preferred range of the first angle is from about 0° to about 4°. The more preferred range of the second angle is from about 3° to about 7°.

Figure 2:
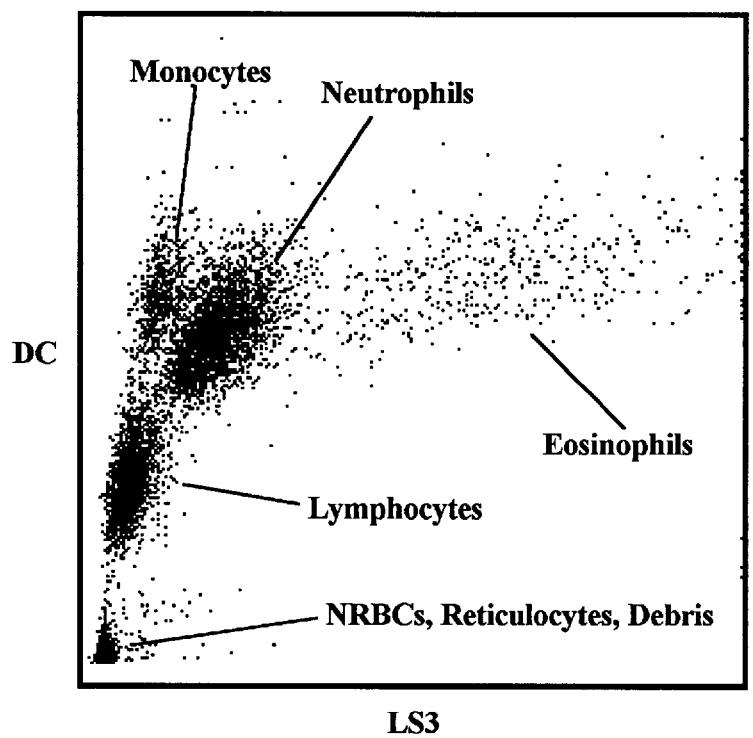

FIG. 1 shows an LS1 (1°–3°) vs. LS2 (4°–6°) scattergram of a clinical whole blood sample, containing 5% reticulocytes, processed and analyzed following the procedure described in Example I. In this scattergram reticulocytes form a cluster which clearly distinguishes from red blood cell debris (below) and leukocytes (above, but out of the scope of this scattergram). This scattergram depicts the cell populations below lymphocyte population on a regular DC scale, a region usually considered as a debris region as shown in FIG. 2.

Figure 3:
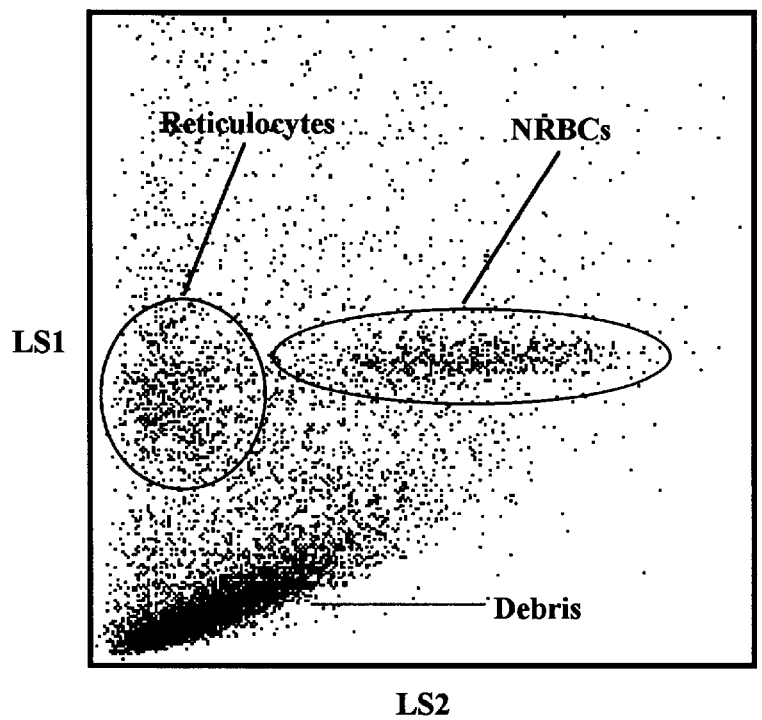

FIG. 3 shows a scattergram of a clinical sample containing reticulocytes and also nucleated red blood cells (NRBC), which is another type of immature red blood cells. The sample was analyzed using the same procedure. The figure shows an additional cluster at the right side of the reticulocytes in the LS1 vs. LS2 scattergram, which corresponds to the NRBCS. The two immature red blood cell populations are separated in this two-dimensional scattergram.

The differentiation of reticulocytes by low angle light scatters (LS1 and LS2) is simple and straightforward. It utilizes a regular two-dimensional dotplot, or scattergram, to distinguish reticulocytes from other cell types. The method does not require nuclear staining or fluorescence detection.

In a second embodiment of the present invention, a differential analysis of leukocytes can be performed together with the differentiation of reticulocytes, using the same lytic reagent system and one sample preparation, in a one-step measurement using electronic and optical analysis. The electronic and optical analyses include light scatter and impedance measurements. The DC impedance measurement device used for leukocyte analysis by an automated hematology analyzer is known to those skilled in the art and is generally described in U.S. Pat. No. 5,125,737, to Rodriguez et al., which is hereby incorporated by reference in its entirety. For diffieriential analysis of reticulocytes and leukocytes, a light scatter detector capable of detecting low and medium angle light scatter signals from a particle or a cell passing the flow cell is used.

In FIG. 1, the leukocytes are out of the range of displayed LS1 vs. LS2 scattergram; they are not shown in the figure. However, the sample analysis for leukocyte differentiation and reticulocyte differentiation can be performed in a one-step measurement. The data analysis for both purposes can be performed simultaneously using different parameters obtained from the one-step measurement.

FIG. 2 shows four distinct clusters of leukocyte subpopulations, lymphocytes, monocytes, neutrophils and eosinophils of a whole blood sample in a DC vs. LS3 (medium angle, from about 24° to about 35°) scattergram. The sample was processed in one sample preparation and analyzed simultaneously with reticulocyte differentiation.

The method of the present invention, for the first time, reports the differentiation of reticulocytes without using nuclear stain and fluorescence.

The method of this invention can be further understood by reference to the following examples. However, it will be appreciated that the invention is not limited to the described examples.

EXAMPLE I

To 28 μl of an EDTA-anticoagulated clinical whole blood sample 417 μl of a lytic reagent comprising 0.18% formic acid, 2% of ethoxylated long chain amine represented by formula:

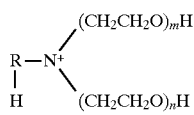

wherein R is stearyl and m+n is equal to 27, 1.4% of Plurafac A38 as a solubilizer and preservatives were added and mixed in a mixing chamber on an experimental hematology analyzer for about 4 seconds. Then 180 μl of a stabilizing reagent comprising 1.4% NaCl, 3.2% $Na_2SO_4$ and 0.66 % $Na_2CO_3$, and having a pH of 11.0 was added and mixed to retard the lytic reaction.

Ten seconds after the addition of the stabilizing reagent the sample mixture was delivered to a focused flow cell with a sheath fluid, ISOTON® III diluent (Coulter Corporation, Miami, Fla.) on an experimental hematology analyzer equipped with DC and light scatter detectors. The light scatter detector detects light scatter signals from a cell passing the flow cell at several ranges of angles, i.e., from about 1° to about 3° (LSI), from about 4° to about 6° (LS2), from about 24° to about 35° (LS3), and higher angles.

The resultant scattergram is illustrated in FIG. 1. FIG. 1 shows a cluster of reticulocytes distinguished from red cell debris (below) and leukocytes (above, but out of the scope of this scattergram) in a LS1 vs. LS2 scattergram.

EXAMPLE II

A fresh normal whole blood sample was analyzed using the same reagents and procedure described in Example I. The sample mixture was analyzed simultaneously in the flow cell on the same hematology analyzer used in Example I for leukocyte differentiation and reticulocyte analysis. FIG. 2 is an obtained DC vs. LS3 scattergram, which shows four distinct clusters of leukocyte subpopulations, lymphocytes, monocytes, neutrophils and eosinophils.

EXAMPLE III

The procedure and reagents described in Example I were used for analysis of a clinical whole blood sample containing reticulocytes and also NRBCS. FIG. 3 is the obtained LS1 vs. LS2 scattergram, which shows an additional cluster at the right side of the reticulocytes corresponding to NRBCs. The two immature red blood cell populations are separated in this LS1 vs. LS2 scattergram.

The invention has been described with reference to particularly preferred embodiments. It will be appreciated, however, that various changes can be made without departing from the spirit of the invention, and such changes are intended to fall within the scope of the claims.

What is claimed is:

1. A method for differentiating reticulocytes comprising:
   (a) exposing a blood cell sample to a reagent system to lyse mature red blood cells; and
   (b) analyzing said sample in a flow cell by measuring low angle light scatter signal detected in less than 10° to differentiate reticulocytes from other cell types.

2. The method of claim 1, wherein said measuring low angle light scatter signal is performed using two low angles of light scatter signals detected in less than 10°.

3. The method of claim 2, wherein said one low angle light scatter signal is in a range from about 0° to about 4°.

4. The method of claim 3, wherein said another low angle light scatter signal is in a range from about 3° to about 7°.

5. A method for differentiating reticulocytes and leukocyte subpopulations comprising:
   (a) exposing a blood cell sample to a reagent system to lyse mature red blood cells; and
   (b) analyzing said sample in a flow cell by DC and light scatter measurements to differentiate reticulocytes and leukocyte subpopulations.

6. The method of claim 5, wherein said light scatter measurement for differentiating reticulocytes is performed using two low angles of light scatter signals detected in less than 10°.

7. The method of claim 6, wherein said one low angle light scatter signal is in a range from about 0° to about 4°.

8. The method of claim 7, wherein said another low angle light scatter signal is in a range from about 3° to about 7°.

9. The method of claim 5, wherein said leukocyte subpopulations are selected from the group consisting of lymphocytes, monocytes, neutrophils and eosinophils.

* * * * *